(12) United States Patent
Baek et al.

(10) Patent No.: US 10,238,800 B2
(45) Date of Patent: Mar. 26, 2019

(54) ELECTRONIC DEVICE AND METHOD OF OPERATING ELECTRONIC DEVICE

(71) Applicant: SAMSUNG ELECTRONICS CO., LTD., Suwon-si (KR)

(72) Inventors: Jae-hyun Baek, Suwon-si (KR); Sung-hoon Moon, Suwon-si (KR); Jin-ha Seong, Seoul (KR); Geon-ho Yoon, Seoul (KR); Wan-hyoung Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 15/819,119

(22) Filed: Nov. 21, 2017

(65) Prior Publication Data

US 2018/0140771 A1    May 24, 2018

Related U.S. Application Data

(60) Provisional application No. 62/424,651, filed on Nov. 21, 2016.

(30) Foreign Application Priority Data

Nov. 3, 2017    (KR) .................. 10-2017-0146174

(51) Int. Cl.
*A61M 5/172* (2006.01)
*A61M 5/14* (2006.01)
(Continued)

(52) U.S. Cl.
CPC .......... *A61M 5/172* (2013.01); *A61M 5/1415* (2013.01); *G06F 19/3481* (2013.01);
(Continued)

(58) Field of Classification Search
CPC ............... A61M 5/16845; A61M 5/168; G01F 23/0076
See application file for complete search history.

(56) References Cited

U.S. PATENT DOCUMENTS

2003/0048185 A1    3/2003   Citrenbaum et al.
2009/0229374 A1    9/2009   Carlisle et al.
(Continued)

FOREIGN PATENT DOCUMENTS

KR    10-2007-0093238 A    9/2007
KR    10-2012-0053187 A    5/2012
(Continued)

OTHER PUBLICATIONS

Communication dated Mar. 5, 2018 issued by the International Searching Authority in counterpart International Patent Application No. PCT/KR2017/013220 (PCT/ISA/220, PCT/ISA/210 & PCT/ISA/237).

*Primary Examiner* — Hongmin Fan
(74) *Attorney, Agent, or Firm* — Sughrue Mion, PLLC

(57) ABSTRACT

An electronic device and a method of operating the electronic device are provided. The method includes sensing a weight of an intravenous (IV) fluid injected into a user; measuring a time remaining until injection of the IV fluid is completed, based on the sensed weight of the IV fluid; determining whether the measured remaining time is equal to or less than a predetermined value; and transmitting an alarm signal indicating an injection state of the IV fluid to an external device based on a result of the determining.

15 Claims, 14 Drawing Sheets

(51) Int. Cl.
 *G06F 19/00* (2018.01)
 *G16H 10/60* (2018.01)
(52) U.S. Cl.
 CPC . *A61M 2205/18* (2013.01); *A61M 2205/3393* (2013.01); *A61M 2205/50* (2013.01); *A61M 2205/502* (2013.01); *A61M 2205/581* (2013.01); *A61M 2205/582* (2013.01); *A61M 2230/63* (2013.01); *G16H 10/60* (2018.01)

(56) References Cited

U.S. PATENT DOCUMENTS

2011/0205074 A1* 8/2011 Feng .................. A61M 5/1414
 340/613
2016/0287785 A1 10/2016 Isaacson et al.

FOREIGN PATENT DOCUMENTS

| | | |
|---|---|---|
| KR | 10-1230772 B1 | 2/2013 |
| KR | 10-2015-0072669 A | 6/2015 |
| KR | 10-2016-0059499 A | 5/2016 |
| KR | 10-1622157 B1 | 5/2016 |
| KR | 10-1624103 B1 | 5/2016 |
| KR | 10-2016-0097397 A | 8/2016 |
| WO | 2016/077534 A1 | 5/2016 |

\* cited by examiner

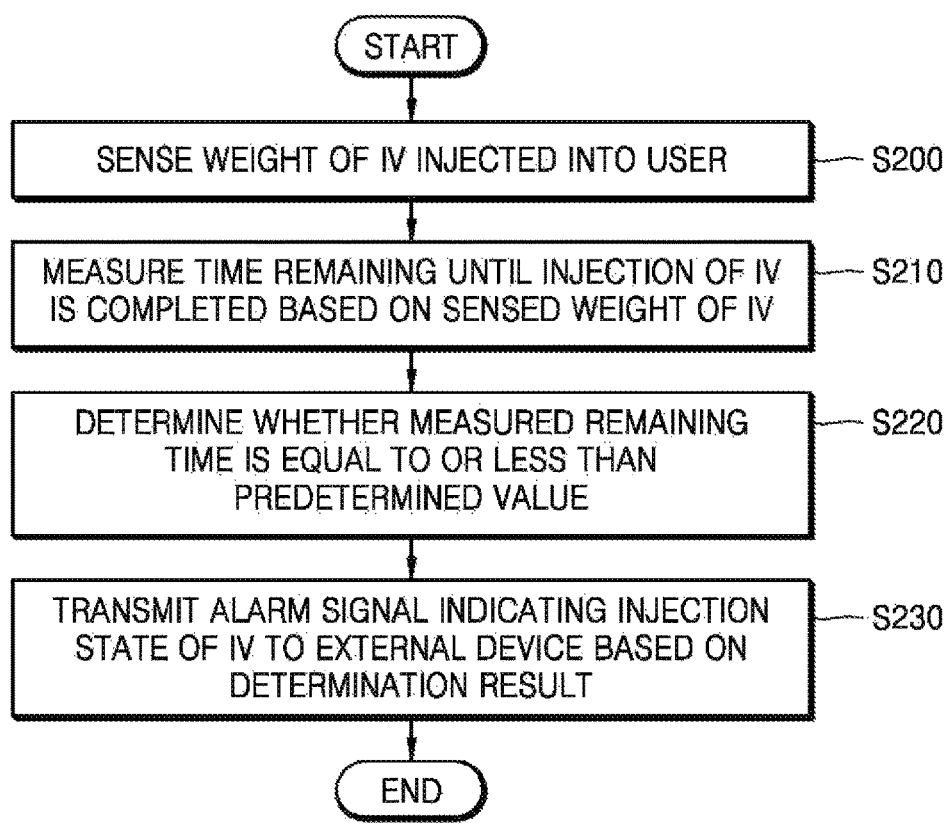

ELECTRONIC DEVICE AND METHOD OF OPERATING ELECTRONIC DEVICE

CROSS-REFERENCE TO RELATED APPLICATIONS

This application claims the priority from U.S. Provisional Application No. 62/424,651, filed on Nov. 21, 2016, in the U.S. Patent and Trademark Office and Korean Patent Application No. 10-2017-0146174, filed on Nov. 3, 2017, in the Korean Intellectual Property Office, the disclosures of which are incorporated herein in their entireties by reference.

BACKGROUND

1. Field

Example embodiments relate to an electronic device and a method of operating the electronic device, and more specifically, to a device and a method for providing information about an injection state of intravenous (IV) fluid injected into a user.

2. Description of the Related Art

A conventional IV pole provides mechanical functions such as a function to hold an IV fluid bag, a function to provide a support for a user to depend on, and a function to provide mobility during IV administration. Accordingly, when the user wants to know information about an IV injection state, the user may obtain the information about the IV injection state from a medical staff member. However, since the IV pole is provided to the user for a certain period of time during an IV injection, it may be easy to determine a state of the user or an amount of exercise performed by the user in real time. Therefore, in order to use the IV pole more efficiently, there is a need for a method of providing information about the state of the user by sensing the amount of exercise performed by the user, the IV injection state, etc.

SUMMARY

One or more example embodiments provide an electronic device for providing information about an injection state of intravenous (IV) administration by sensing a weight of IV fluid injected into a user and a method of operating the electronic device.

One or more example embodiments provide an electronic device for measuring an amount of exercise performed by a user and providing information about the measured amount of exercise by sensing acceleration, and a method of operating the electronic device.

According to an aspect of an example embodiment, there is provided a method of operating an electronic device, the method including sensing a weight of an intravenous (IV) fluid injected into a user, measuring a time remaining until injection of the IV fluid is completed, based on the sensed weight of the IV fluid, determining whether the measured remaining time is equal to or less than a predetermined value, and transmitting an alarm signal indicating an injection state of the IV fluid to an external device in response to the measured remaining time being determined to be equal to or less than the predetermined value.

The method may further include receiving prescription information with respect to the user from a server, and determining a type of the IV fluid by comparing the received prescription information and the sensed weight of the IV fluid.

The method wherein the received prescription information may include a plurality of IV fluids prescribed to the user, and wherein the determining of the type of the IV fluid may include, among the plurality of IV fluids from the received prescription information, in response to an external input of selecting one of two or more IV fluids having the same weight as the sensed weight of the IV fluid injected into the user, determining the type of the IV fluid injected into the user as the selected IV fluid.

The method may further include outputting a user interface (UI) indicating information about the injection state of the IV fluid.

The method may further include obtaining acceleration data by sensing acceleration of the electronic device, determining whether a number of pieces of acceleration data having a magnitude equal to or greater than a threshold value among a plurality of pieces of acceleration data obtained during a predetermined time is equal to or greater than a predetermined number, and measuring an amount of exercise performed by the user based on the number of pieces of acceleration data determined to have a magnitude equal to or greater than the predetermined number.

The method wherein the measuring of the amount of exercise performed by the user may include measuring the amount of exercise performed by the user based on a difference between a first point in time at which the number of pieces of acceleration data having the magnitude equal to or greater than the threshold value is equal to or greater than the predetermined number, and a second point in time at which the number of pieces of acceleration data having the magnitude equal to or greater than the threshold value is less than the predetermined number.

The method may further include sensing a weight of a discharge liquid discharged from the user, determining whether the sensed weight of the discharge liquid is equal to or greater than a predetermined weight, and transmitting an alarm signal indicating a discharge state of the discharge liquid to the external device based on the sensed weight being determined to be equal to or greater than the predetermined weight.

According to another aspect of an example embodiment, there is provided an electronic device including a sensor configured to sense a weight of an intravenous (IV) fluid injected into a user, a communicator, and a processor configured to measure a time remaining until injection of the IV fluid is completed based on the sensed weight of the IV fluid, determine whether the measured remaining time is equal to or less than a predetermined value, and control the communicator to transmit an alarm signal indicating an injection state of the IV fluid to an external device in response to the measured time being determined to be equal to or less than the predetermined value.

The processor of the electronic device may be further configured to control the communicator to receive prescription information with respect to the user from a server, and determine a type of the IV fluid by comparing the received prescription information and the sensed weight of the IV fluid.

The received prescription information may include a plurality of IV fluids prescribed to the user, and the processor may be further configured to, among the plurality of IV fluids included in the received prescription information, in response to an external input of selecting one of two or more IV fluids having the same weight as the sensed weight of the IV fluid injected into the user, determine the type of the IV fluid injected into the user as the selected IV fluid.

The electronic device may further include a display configured to output a user interface (UI) indicating information about the injection state of the IV fluid.

The sensor of the electronic device may be further configured to obtain acceleration data by sensing acceleration of the electronic device, and the processor may be further configured to determine whether a number of pieces of acceleration data having a magnitude equal to or greater than a threshold value among a plurality of pieces of acceleration data obtained during a predetermined time is equal to or greater than a predetermined number, and measure an amount of exercise performed by the user based on the number of pieces of acceleration data determined to have a magnitude equal to or greater than the predetermined number.

The processor may be further configured to measure the amount of exercise performed by the user based on a difference between a first point in time at which the number of pieces of acceleration data having the magnitude equal to or greater than the threshold value is equal to or greater than the predetermined number, and a second point in time at which the number of pieces of acceleration data having the magnitude equal to or greater than the threshold value is less than the predetermined number.

The sensor of the electronic device may be further configured to sense a weight of a discharge liquid discharged from the user, and the processor may be further configured to determine whether the sensed weight of the discharge liquid is equal to or greater than a predetermined weight, and transmit an alarm signal indicating a discharge state of the discharge liquid to the external device in response to the sensed weight being determined to be equal to or greater than the predetermined weight.

The program for executing the method of operating the electronic device on a computer may be recorded on a non-transitory computer-readable recording medium.

BRIEF DESCRIPTION OF THE DRAWINGS

The above and/or other aspects will become apparent and more readily appreciated from the following description of the example embodiments, taken in conjunction with the accompanying drawings in which:

FIG. 2 is a flowchart explaining a method of operating an electronic device according to an example embodiment;

DETAILED DESCRIPTION

Hereinafter, various example embodiments of the present disclosure will be described in greater detail with reference to the accompanying drawings. These example embodiments are described in sufficient detail to enable those skilled in the art to practice the inventive concept, and it is to be understood that the example embodiments are not intended to limit the present disclosure to particular modes of practice, and it is to be appreciated that all modification, equivalents, and alternatives that do not depart from the spirit and technical scope of the present disclosure are encompassed in the present disclosure.

As used herein, "a," "an" and "the" are intended to include the plural forms as well, unless the context clearly indicates otherwise. Further, when a certain part is "connected" to another part, it should be understood that the certain part may be "directly connected" to another part or "electrically connected" via another element in the middle. Also, when a certain part "includes" or "has" a certain component, this indicates that the part may further include another component instead of excluding another component unless there is different disclosure. As used herein, the term "and/or" includes any and all combinations of one or more of the associated listed items. Expressions such as "at least one of," when preceding a list of elements, modify the entire list of elements and do not modify the individual elements of the list.

Figure 1:
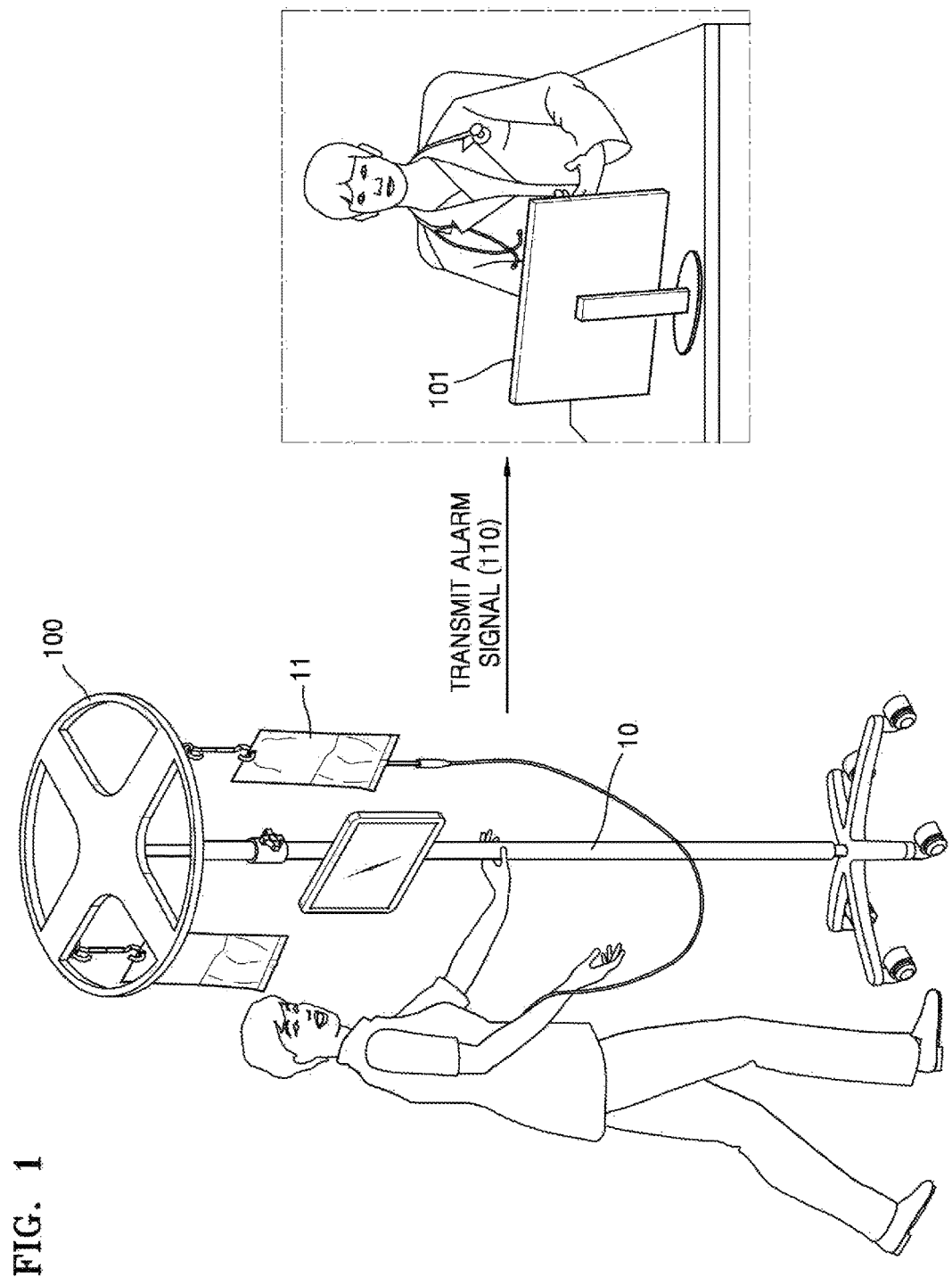
FIG. 1 is a diagram of an example in which an electronic device provides information about intravenous (IV) fluid injected into a user according to example embodiments.

FIG. 1 is a diagram of an example in which an electronic device 100 provides information about intravenous (IV) fluid 11 injected into a user according to example embodiments.

The electronic device 100 may include a device that provides information about an injection state of the IV fluid 11 (hereinafter referred to as "IV 11") injected into the user. For example, as shown in FIG. 1, the electronic device 100 may be implemented to operate by being coupled to an IV pole 10. Alternatively, according to an example embodiment, the electronic device 100 may be a component of the IV pole 10, and may be implemented integrally with the IV pole 10, but is not limited thereto.

Referring to FIG. 1, the IV pole 10 may be used to hold the IV 11 injected into the user, and may provide support for the user when the user moves. Since the IV pole 10 may be provided to the user for a certain period of time during which the user is injected with the IV 11, it may be easier to obtain information such, for example, as the injection state of the IV 11 or an amount of exercise of the user. If the electronic device 100 combined with the IV pole 10 may provide the information such as the injection state of the IV 11 or the amount of exercise of the user in real time, the user and a medical staff may more easily determine the information such as the injection state of the IV 11.

Also, the electronic device 100 according to an example embodiment may determine whether the time remaining until an injection of the IV 11 is completed is equal to or less than a predetermined value, and, based on a determination result, may transmit an alarm signal 110 to an external device 101 monitored by the medical staff. Thus, the electronic device 100 may make it easier for the medical staff to determine when the IV 11 should be removed from the user.

Hereinafter, a method of operating the electronic device 100 will be described in more detail with reference to FIG. 2.

FIG. 2 is a flowchart for explaining a method of operating the electronic device 100 according to an example embodiment.

In operation S200, the electronic device 100 may sense a weight of the IV 11 injected into a user. For example, the electronic device 100 may sense the weight of the IV 11 using a weight sensor 111 included in the electronic device 100. For example, the weight sensor 111 may amplify a voltage variation value that varies depending on the weight of the IV 11 or a discharge fluid, convert the amplified voltage variation value into a digital signal, and may sense the weight of the IV 11 or the discharge fluid based on the converted digital signal.

Also, the electronic device 100 according to an example embodiment may sense the weight of the discharge fluid discharged from the user as well as the IV 11 injected into the user, and may sense an acceleration of the electronic device 100 when the electronic device 100 moves. For example, the electronic device 100 may sense the acceleration of the electronic device 100 using an acceleration sensor.

In operation S210, the electronic device 100 may measure the time remaining until an injection of the IV 11 is completed, based on the sensed weight of the IV 11.

The electronic device 100 according to an example embodiment may sense an initial weight of the IV 11 when the IV 11 is connected to the electronic device 100 and may sense the weight of the IV 11 in a predetermined period unit. Further, the electronic device 100 may calculate a speed at which the IV 11 is injected by measuring a variation in the weight of the IV 11 over a unit time. The electronic device 100 may measure the time remaining until the injection of the IV 11 is completed complete based on the weight of the IV 11 and the injection speed of the IV 11.

In operation S220, the electronic device 100 may determine whether the time remaining until the injection of the IV 11 is completed is equal to or less than a predetermined value. When the injection of the IV 11 is completed, a medical staff may need to remove the IV 11 connected to the electronic device 100. Therefore, if the time remaining until the injection of the IV 11 is equal to or less than the predetermined value, the medical staff may need to be informed of the time left for removing the IV 11. The predetermined value may vary depending on an internal setting or an external setting of the electronic device 100. For example, the predetermined value may be set to 5 minutes, and the electronic device 100 may determine whether the time remaining until the injection of the IV 11 is completed is 5 minutes or less, but example embodiments are not limited thereto.

The electronic device 100 according to an example embodiment may sense the acceleration of the electronic device 100 to obtain acceleration data, and measure an amount of exercise of the user based on the obtained acceleration data. An example embodiment of a method of measuring the amount of exercise of the user will be described later with reference to FIG. 8. Further, the electronic device 100 may output the measured amount of exercise of the user together with information about an injection state of the IV 11.

The electronic device 100 according to an example embodiment may sense a weight of a discharge fluid (for example, urine, secretion, body fluids, etc.) discharged from the user as well as the weight of the IV 11 injected into the user, and may determine whether the weight of the discharge fluid is equal to or greater than a predetermined value.

In operation S230, the electronic device 100 may transmit, to the external device 101, an alarm signal indicating the injection state of the IV 11 based on a determination result.

The electronic device 100 according to an example embodiment may transmit the alarm signal indicating the injection state of the IV 11 to the external device 101 since the electronic device 100 determines that the time remaining until the injection of the IV 11 is completed is less than the predetermined value. For example, the external device 101 may include a device used by the medical staff to monitor a status of a patient in real time. The electronic device 100 may transmit the alarm signal indicating the injection state of the IV 11 to the external device 101, such that the medical staff may more quickly and easily check the injection state of the IV 11 for the user.

The alarm signal indicating the injection state of the IV 11 may include at least from among of a signal indicating the time remaining until the injection of the IV 11 is completed, a signal indicating an estimated time when the injection of the IV 11 is completed, and a signal requesting the medical staff to remove the IV 11 but example embodiments are not limited thereto.

Also, the electronic device 100 according to an example embodiment may transmit an alarm signal indicating that the weight of the discharge fluid discharged from the user is equal to or greater than the predetermined value to the external device 101.

The electronic device 100 according to an example embodiment may output a user interface (UI) indicating information about the injection state of the IV 11. For example, when the electronic device 100 is implemented integrally with the IV pole 10, the electronic device 100 may further include a display including a display UI. At this time, the electronic device 100 may output the UI indicating the information about the injection state of the IV 11 on the display of the electronic device 100 in real time.

Further, according to an example embodiment, when the electronic device 100 is implemented to operate by being coupled to the IV pole 10, or when the electronic device 100 is implemented to be used by replacing a part of the IV pole 10, the electronic device 100 may output the UI indicating the information about the injection state of the IV 11 through a mobile device of the user. For example, the mobile device of the user may be provided with an application for monitoring the injection state of the IV 11, and may transmit and receive the information about the injection state of the IV 11 using wireless communication or by being physically connected with the electronic device 100, but example embodiments are not limited thereto.

The electronic device 100 according to an example embodiment may output on the UI information about the injection state of the IV 11 and transmit the alarm signal to the external device 101 when the time remaining until the injection of the IV 11 is completed is equal to or less than the predetermined value, thereby allowing the user and the medical staff to more easily and quickly check the injection state of the IV 11 with respect to the user. Further, the electronic device 100 may allow the medical staff to more accurately determine when the IV 11 should be removed.

Figure 3A:
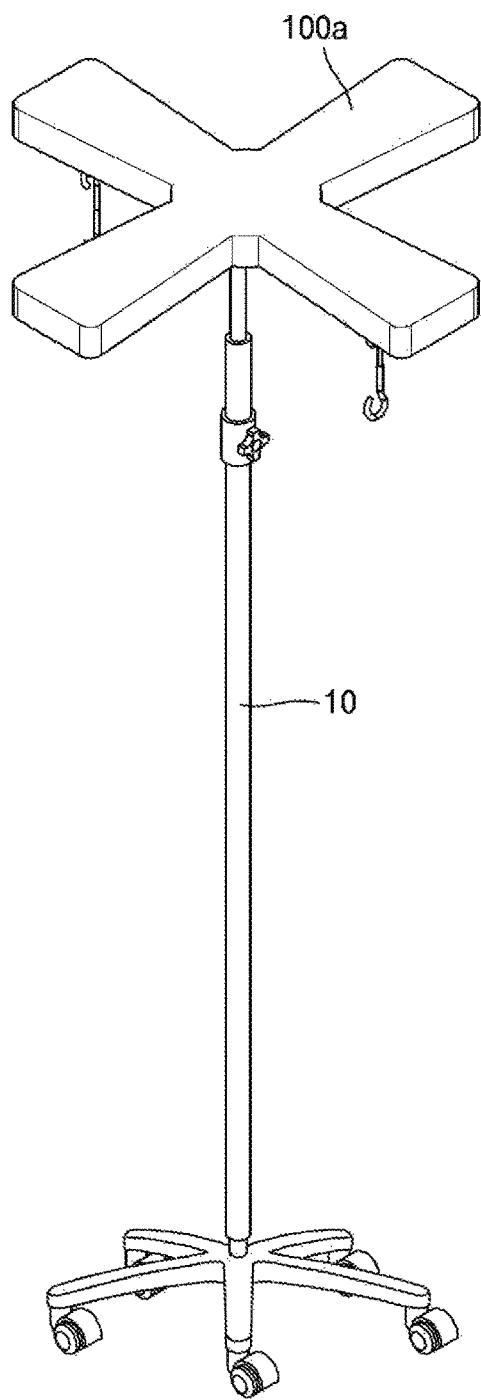
FIGS. 3A to 3C are diagrams illustrating various implementation examples of electronic devices according to example embodiments.
Figure 3B:
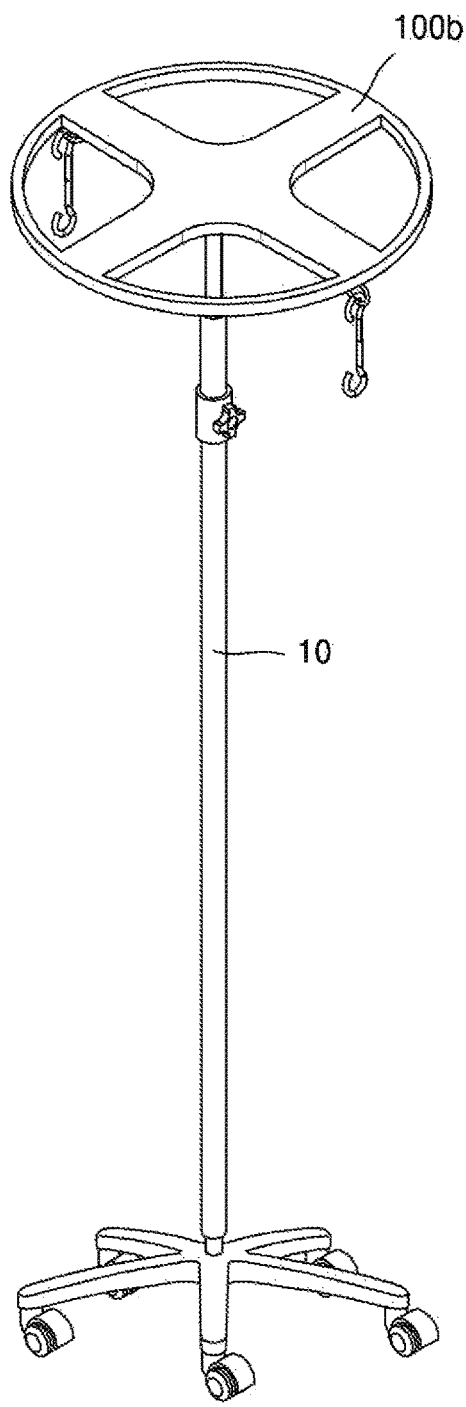
Figure 3C:
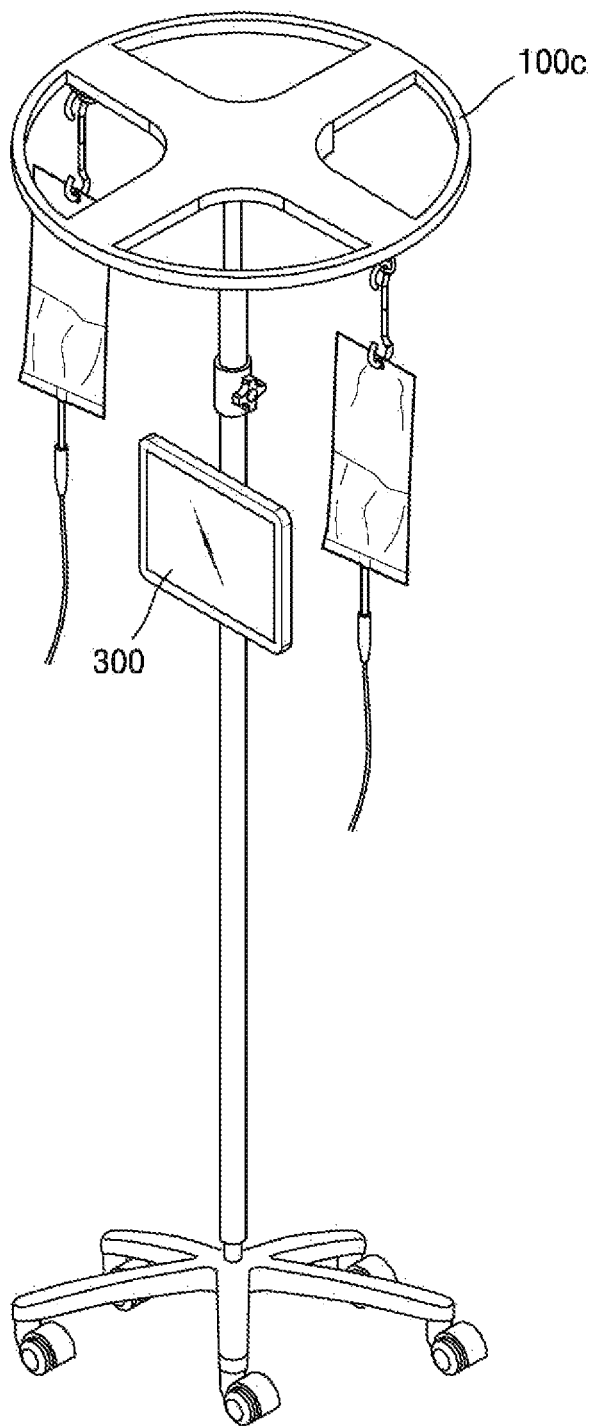

FIGS. 3A to 3C are diagrams illustrating various implementation examples of electronic devices 100a, 100b, and 100c according to example embodiments.

The electronic device 100a according to an example embodiment may be implemented to operate by being coupled to the IV pole 10. For example, referring to FIG. 3A, an upper end portion of the IV pole 10 may be implemented in a cross shape to hold a plurality of IV 11, and the electronic device 100a may also be implemented in the cross shape such that the electronic device 100a may be used by being coupled to the IV pole 10.

As shown in FIG. 3A, when the electronic device 100a is implemented as being coupled to the IV pole 10, the electronic device 100a may further include an IV holder for holding the IV 11. For example, the IV holder may be in the form of a ring capable of holding a bag containing IV 11, but example embodiments are not limited thereto. Also, when the electronic device 100a is implemented as being coupled to the IV pole 10, since the existing IV pole 10 may be recycled, the electronic device 100a may be more easily applied. Also, since the existing IV pole 10 may be recycled, the electronic device 100a may have the same strength of the existing IV pole 10 capable of supporting a weight of the IV 11.

Also, the electronic device 100b according to an example embodiment may be implemented to replace a part of the IV pole 10. For example, referring to FIG. 3B, the electronic device 100b may be implemented to replace the upper end portion of the IV pole 10.

Also, as shown in FIG. 3C, the electronic device 100c according to an example embodiment may be implemented integrally with the IV pole 10, and may further include a display 300 according to an example embodiment. When the electronic device 100c is implemented integrally with the IV pole 10, the electronic device 100c may further include a barcode reader for identifying a plurality of users, and include a wireless charging module to more uniformly supply power to the electronic device 100c. Also, the electronic device 100 according to an example embodiment may be implemented in a separate dongle form. For example, the electronic device 100 may be implemented to operate by being connected to the IV pole 10 and connecting the IV 11 to the electronic device 100.

Hereinafter, an example embodiment where the electronic device 100 is implemented integrally with the IV pole 10 will be described as an example.

Figure 4:
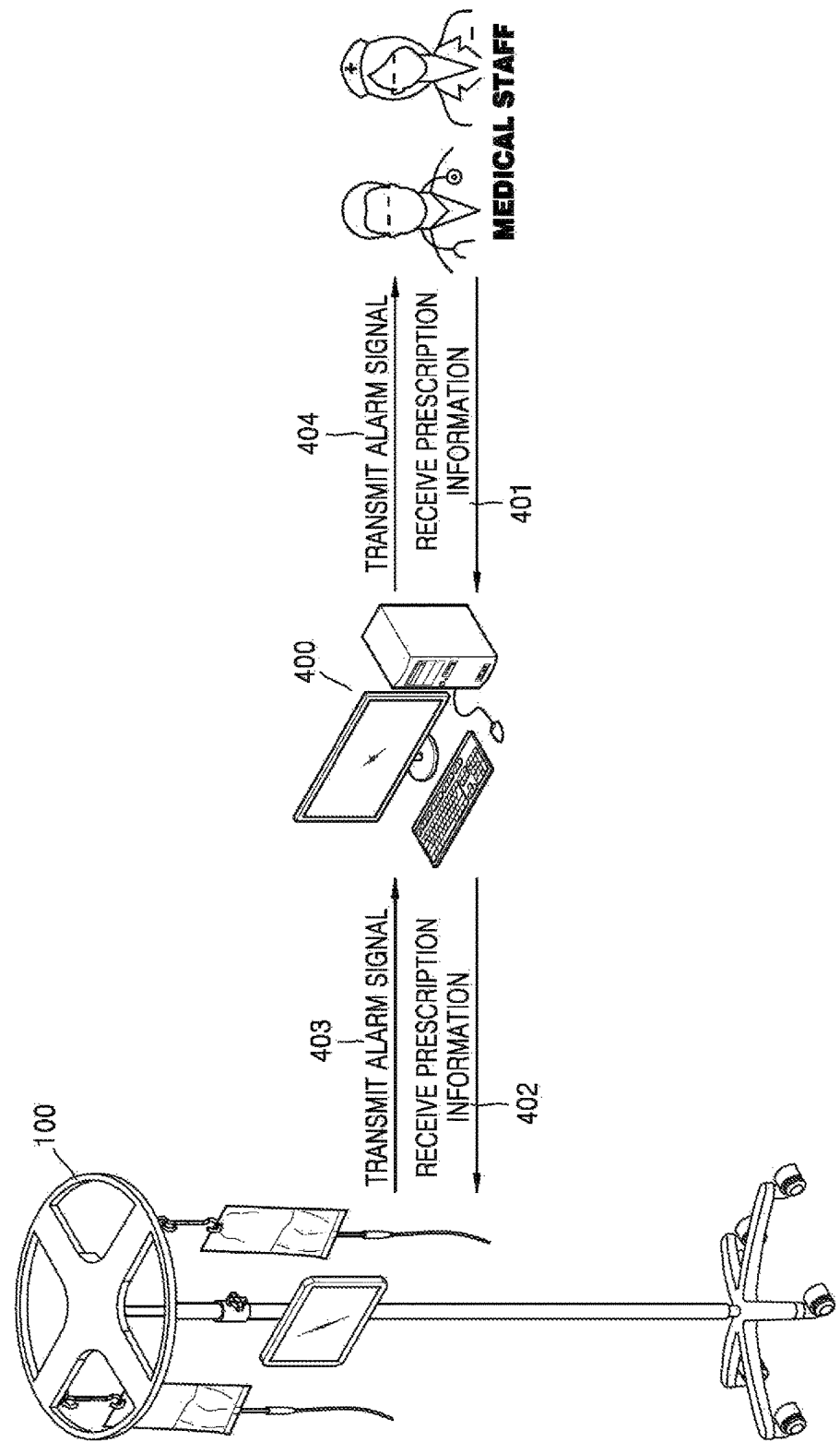
FIG. 4 is a diagram explaining a method by which an electronic device provides information about a status of a user in association with a server, according to an example embodiment.

FIG. 4 is a diagram for explaining a method by which the electronic device 100 provides information about a status of a user in association with a server 400 according to an example embodiment.

The electronic device 100 according to an example embodiment may transmit and receive information about the user to and from the server 400 connected via a network.

Referring to FIG. 4, the server 400 may be, for example, a server of a hospital information system (HIS). For example, the server 400 may store prescription information about the user, medical record information of the user, and information necessary for diagnosing the user in a hospital in a database. For example, if a medical staff prescribes one or more IV fluids to the user and enters prescription information of the user into the external device 101 used by the medical staff, the prescription information may be stored in the server 400, but example embodiments are not limited thereto.

The electronic device 100 according to an example embodiment may receive the prescription information of the user from the server 400. For example, the electronic device 100 may receive the prescription information of the user from the server 400 when an IV 11 is connected to the electronic device 100. The electronic device 100 may confirm a type and a weight of the prescribed IV 11 of the user based on the received prescription information.

Also, the electronic device 100 according to an example embodiment may sense the weight of the IV 11 connected to the electronic device 100. The electronic device 100 may recognize the type of IV 11 connected to the electronic device 100 by comparing an identified weight of the IV 11 and the determined weight of the IV 11 based on the received prescription information. For example, the electronic device 100 may map 1000 mL to 1000 g, but example embodiments are not limited thereto, and may vary depending on settings. For example, when the prescribed IV 11 of the user is glucose of 1000 mL and analgesic of 150 mL, if the sensed weight of the IV 11 is 1000 g, the electronic device 100 may recognize the sensed IV 11 as glucose. Further, if the sensed weight of the IV 11 is 150 g, the electronic device 100 may determine the sensed IV 11 as analgesic.

Figure 5A:
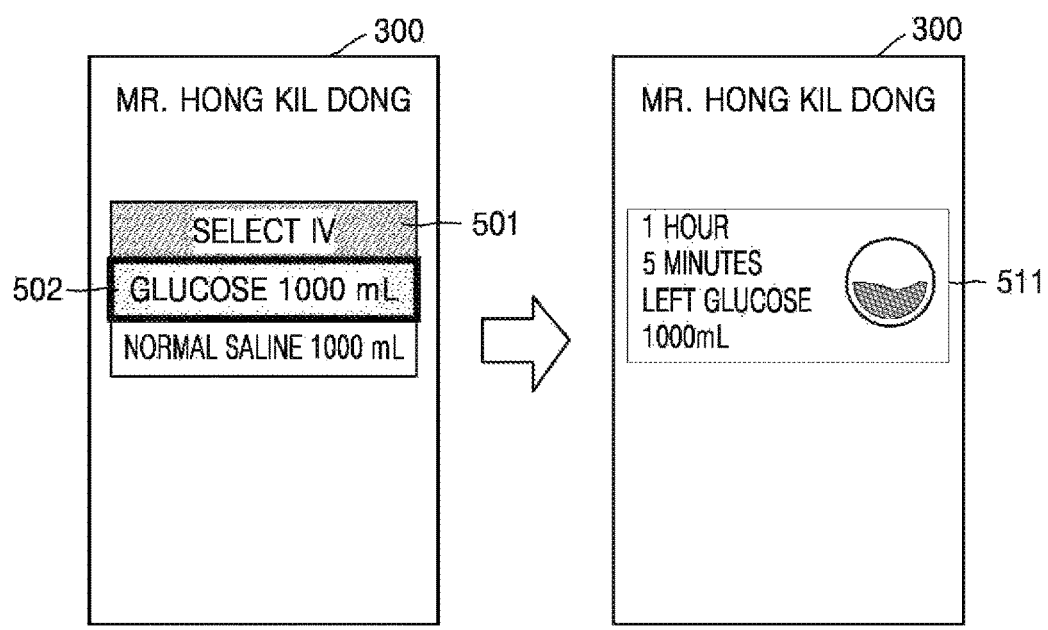
FIGS. 5A to 5C are diagrams explaining a method by which an electronic device outputs a recognized type of an IV fluid based on prescription information of a user according to an example embodiment.
Figure 5B:
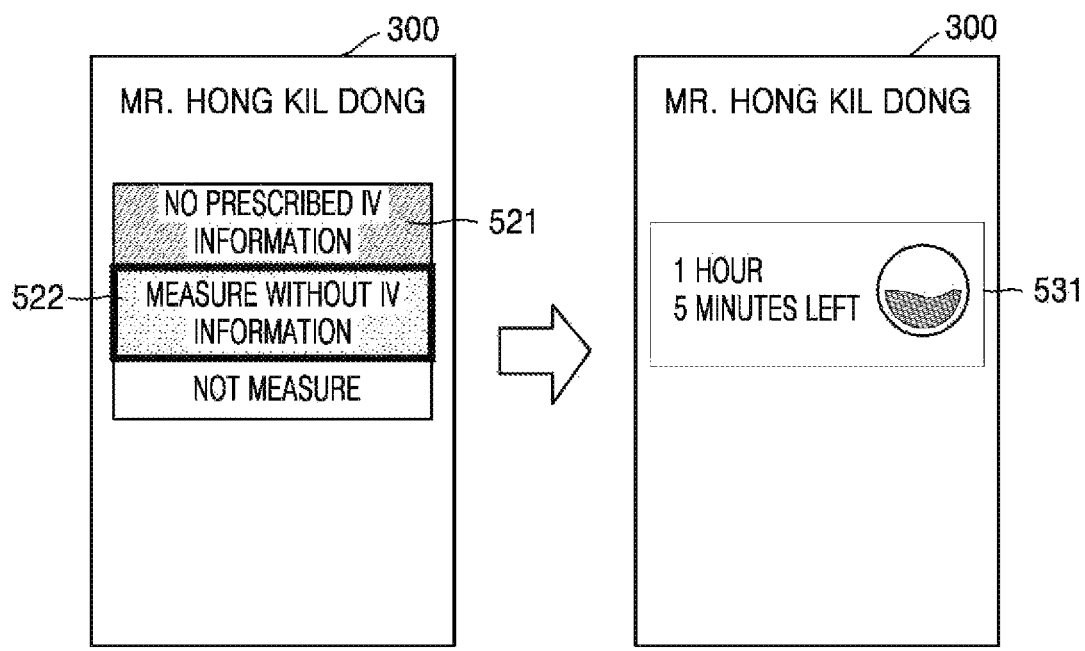
Figure 5C:
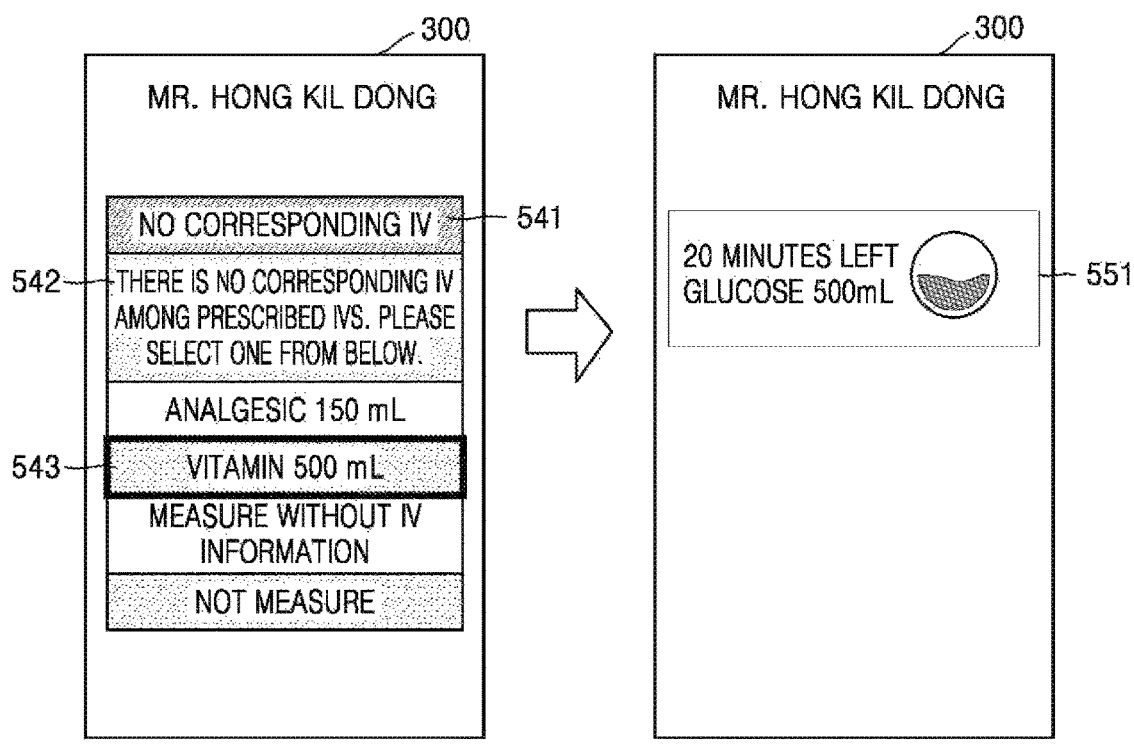

FIGS. 5A to 5C are diagrams for explaining a method by which the electronic device 100 outputs a recognized type of an IV 11 based on prescription information of a user according to an example embodiment.

As described above, the electronic device 100 may recognize the type of the IV 11 connected to the electronic device 100 based on the prescription information of the user and a sensed weight of the IV 11 when the IV 11 is connected to the electronic device 100. The electronic device 100 may identify types and weights of one or more prescribed IV fluids of the user from the prescription information of the user. Also, the electronic device 100 may determine if there is any IV 11 having the same weight as the IV 11 connected to the electronic device 100 among from the one or more prescribed IV fluids. Accordingly, the IV 11 connected to the electronic device 100 may be recognized as an IV fluid having the same weight as the IV 11 connected to the electronic device 100 among the one or more prescribed IVs.

However, when there are a plurality of prescribed IV fluids and two or more IV fluids have the same weight as the sensed weight of the IV 11 among the plurality of prescribed IV fluids, the electronic device 100 may output a UI for selecting the IV 11 connected to the electronic device 100 from the two or more prescribed IV fluids. For example, the user may be prescribed glucose of 1000 mL, normal saline of 1000 mL, and analgesic of 500 mL, and the weight of the IV 11 sensed by the electronic device 100 may be 1000 g. Among three prescribed IV fluids of the user, IV fluid having the same weight as the IV 11 connected to the electronic device 100 are glucose and normal saline. At this time, the electronic device 100 may output the UI for selecting the IV 11 connected to the electronic device 100 from glucose and normal saline.

Referring to FIG. 5A, the electronic device 100 may output a UI 501 for selecting the IV 11 connected to the electronic device 100 from glucose of 1000 mL and normal saline of 1000 mL to a display 300 of the electronic device 100. When an external input 502 of selecting glucose of 1000 mL from glucose of 1000 mL and normal saline of 1000 mL is received, the electronic device 100 may recognize the IV 11 connected to the electronic device 100 as glucose. Further, the electronic device 100 may output a UI 511 indicating the recognized type of the IV 11 and the time remaining until an injection of the IV 11 is completed to the display 300.

Further, according to an example embodiment, the electronic device 100 may not receive the prescription information of the user from a server. For example, the electronic device 100 may not be temporarily connected to the server, or the prescription information of the user may not be stored in the server. If the electronic device 100 does not receive the prescription information of the user from the server, the electronic device 100 may indicate that there is no prescribed IV fluid information, and may output a UI for selecting whether to measure the time remaining until the injection of the IV 11 connected to the electronic device 100 is completed.

For example, referring to FIG. 5B, if the IV 11 is connected to the electronic device 100 and the electronic device 100 fails to receive the prescription information of the user from the server, the electronic device 100 may output a message 521 informing that there is no prescribed IV information to the display 300. The electronic device 100 may also output a UI for selecting whether to measure the time remaining until the injection of the IV 11 is completed, without the information about the IV 11 connected to the electronic device 100. As an external input 522 of selecting whether to measure the remaining time is received, the electronic device 100 may output a UI 531 indicating the time remaining until the injection of the IV 11 connected to the electronic device 100 is completed to the display 300.

Further, according to an example embodiment, among the plurality of prescribed IV fluids of the user, there may be no IV fluid having the same weight as the sensed weight of the IV 11 by the electronic device 100. For example, referring to FIG. 5C, the sensed weight of the IV 11 by the electronic device 100 may be 1000 g, and the plurality of prescribed IV fluids of the user may be analgesic of 150 mL and vitamin of 500 mL. At this time, the electronic device 100 may output, to the display 300, a message 541 informing that there is no IV fluid corresponding to the IV 11 connected to the electronic device 100 among the prescribed IV fluids. Also, the electronic device 100 may output a UI 542 for selecting one of the plurality of prescribed IV fluids of the user, or for selecting whether to measure the remaining time without information about the type of the IV 11.

The electronic device 100 according to an example embodiment may recognize the IV 11 connected to the electronic device 100 as the selected IV fluid when an external input 543 for selecting one of the plurality of prescribed IV fluids of the user is received, and may measure the recognized type of the IV 11 and the time remaining until the injection of the IV 11 is completed. The electronic device 100 may also output a UI 551 indicating the recognized type of the IV 11 and the time remaining until the injection of the IV 11 is completed to the display 300.

According to an example embodiment, when the electronic device 100 does not include the display 300, the electronic device 100 may output information about an injection state of the user through a mobile device of the user connected to the electronic device 100 over a network. At this time, an application for monitoring the injection state of the IV 11 may be installed in the mobile device, and the electronic device 100 may transmit the information about the injection state of the IV 11 to the user through the installed application. Accordingly, the user may confirm the information about the injection state of the IV 11 in real time using the installed application.

Figure 6:
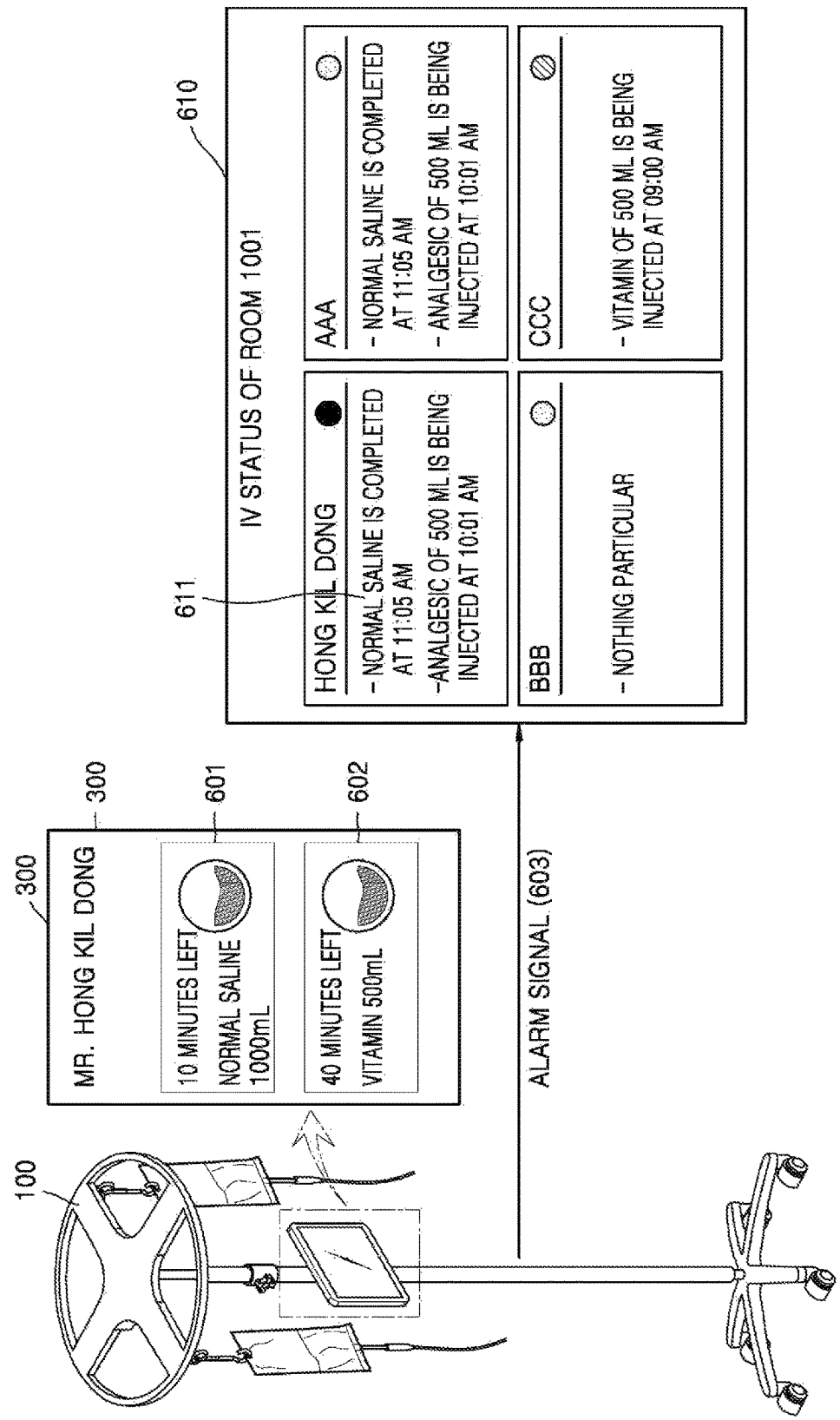
FIG. 6 is a diagram explaining a method by which an electronic device transmits, to an external device, an alarm signal indicating an IV injection state according to an example embodiment.

FIG. 6 is a diagram for explaining a method by which the electronic device 100 transmits an alarm signal 603 indicating an injection state of an IV 11 to an external device according to an example embodiment.

The electronic device 100 according to an example embodiment may sense a weight of the IV 11 connected to the electronic device 100 and measure a time remaining until an injection of the IV 11 is completed based on the sensed weight of the IV 11 and an injection rate of the IV 11. For example, the injection rate of the IV 11 may be calculated based on the sensed weight of the IV 11 in real time. The electronic device 100 may measure a variation in the weight of the IV 11 with respect to a unit time, and calculate the injection rate of the IV 11 based on a result of measurement. Accordingly, the electronic device 100 may determine whether the injection rate of the IV 11 is outside of a predetermined range. If the electronic device 100 senses that the injection rate of the IV 11 changed, the electronic device 100 may transmit the alarm signal 603 to the external device 101.

The electronic device 100 according to an example embodiment may determine whether the remaining time until the injection of the IV 11 is completed is equal to or less than a predetermined value, and may transmit the alarm signal 603 indicating the injection state of the IV 11 to the external device 101 if the electronic device 100 determines that the remaining time is equal to or less than the predetermined value. For example, the alarm signal 603 indicating the injection state of the IV 11 may include at least one of a signal indicating the remaining time until the injection of the IV 11 is completed, a signal indicating an expected time when the injection of the IV 11 is completed, and a signal requesting a medical staff to remove the IV 11, but example embodiments are not limited thereto. The external device 101 monitored by the medical staff may display the alarm signal 603 received from the electronic device 100 on a display 610 of the external device 101. For example, referring to FIG. 6, the external device 101 may output a message 611 informing that an injection of normal saline to a user Kate will be completed at 11:05 am and an injection of analgesic of 500 mL has started at 10:01 am to the display 610 of the external device 101. Accordingly, the medical staff may more easily confirm the injection state of the IV 11 with respect to the user, and may more quickly remove the IV 11 in accordance with the time when the injection of the IV 11 is displayed to be completed.

According to an example embodiment, the external device 101 may receive information about the injection state of the IV 11 from the plurality of electronic devices 100. Further, the external device 101 may receive information about an injection state of an IV 11 of each user from the plurality of electronic devices 100 respectively assigned to a plurality of users, and may display the information about the injection state of the IV 11 of each of the plurality of users on one screen. Accordingly, the medical staff may easily check the injection state of the IV 11 of each of the plurality of users, and may more quickly conduct a necessary action for each user.

The electronic device 100 according to an example embodiment may sense a weight of a discharge liquid (e.g., urine, secretions, body fluids, etc.) discharged from the user as well as the weight of the IV 11 injected to the user. For example, a drain bag that is used to drain deceased secretions from the body of a user after surgery may be connected to the electronic device 100. The electronic device 100 may sense a weight of the drain bag, and when the secretions are discharged to the drain bag, the weight of the drain bag is increased. When the drain bag is filled with the discharge liquid over a certain level, the drain bag may be required to be replaced with a new drain bag. Accordingly, a method of monitoring an amount of the discharge fluid that flows into the drain bag may be required. Therefore, the electronic device 100 may sense the weight of the drain bag containing the discharge liquid, and when it is determined that the weight of the drain bag is equal to or greater than a predetermined value, the electronic device 100 may transmit an alarm signal indicating that the drain bag must be replaced with the new drain bag to an external device 101.

Also, the electronic device 100 according to an example embodiment may output a UI informing the amount of the discharge fluid flowing into the drain bag and the time remaining until the drain bag needs to be replaced, through a mobile device of the user. Thus, the electronic device 100 may allow the medical staff and the user to more easily monitor the amount of the discharge fluid that flows into the drain bag. Further, the electronic device 100 may allow the medical staff to replace the drain bag of the user at an appropriate time.

Figure 7:
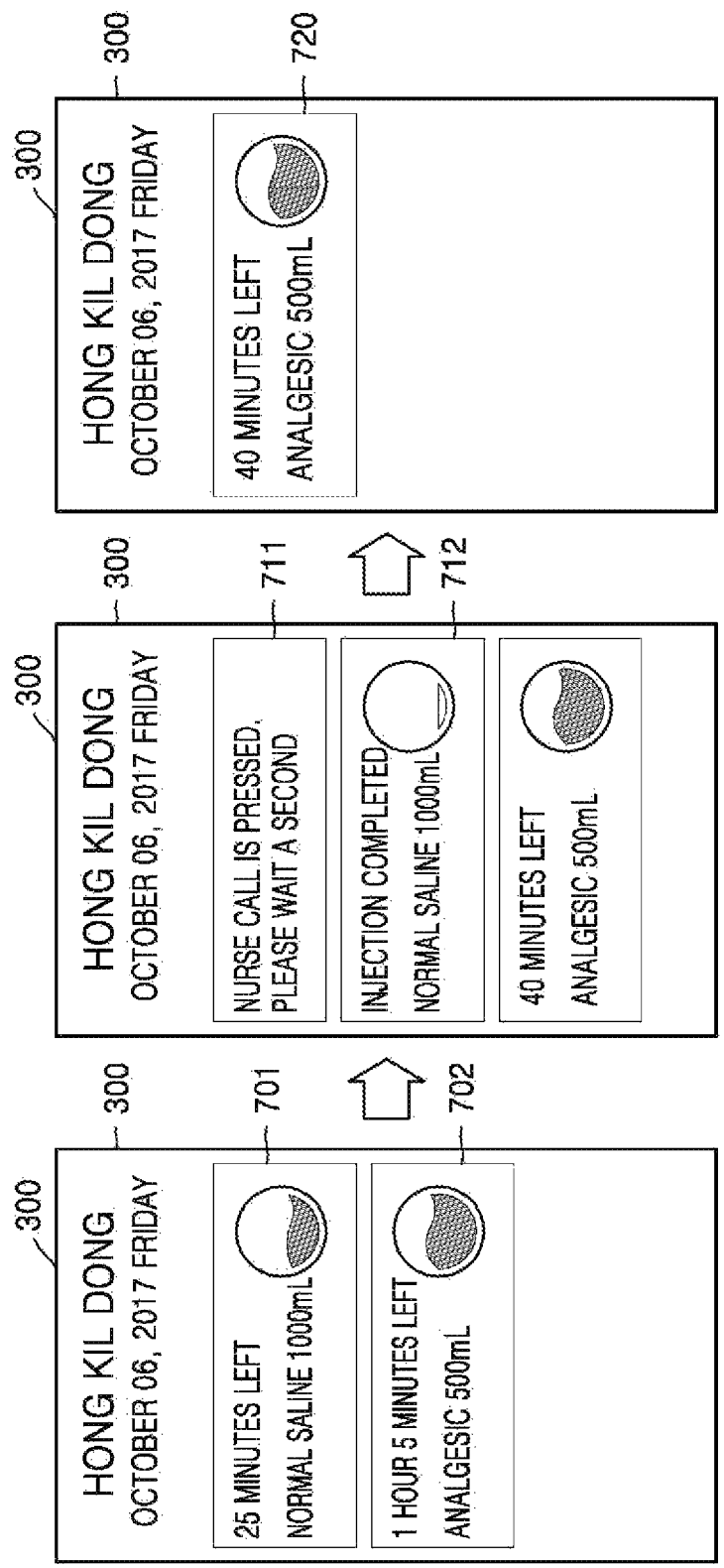
FIG. 7 is a diagram illustrating an example in which an electronic device outputs information indicating an IV injection state in real time according to an example embodiment.

FIG. 7 is a diagram illustrating an example in which an electronic device outputs information indicating an injection state of an IV 11 in real time according to an example embodiment.

The electronic device 100 according to an example embodiment may monitor the injection state of the IV 11 in real time and output an UI indicating the information about the injection state of the IV 11 to the display 300.

Referring to FIG. 7, the electronic device 100 may output, for example, a UI 701 indicating 25 minutes left until an injection of prescribed normal saline of a user is completed, and a UI 702 indicating 1 hour 5 minutes left until an injection of analgesic of 500 mL is completed to the display 300.

The electronic device 100 according to an example embodiment may transmit an alarm signal indicating the injection state of the IV 11 into the external device 101 when it is determined that a time remaining until the injection of the IV 11 is completed is equal to or less than a predetermined value. Further, the electronic device 100 may transmit an alarm signal indicating that the injection of the IV 11 has been completed to the external device 101 when the injection of the IV 11 is completed. Referring to FIG. 7, the electronic device 100 may output a UI 712 indicating that an injection of normal saline of 1000 mL is completed, and may also output a message 711 informing that a medical staff has been called.

The electronic device 100 according to an example embodiment may not any longer output a message indicating the injection state of the IV 11 since the IV 11 of which injection has been completed is removed by the medical staff. Referring to FIG. 7, when the injection of normal saline of 1000 mL is completed and the normal saline is removed by a nurse, the electronic device 100 may no longer output an UI indicating the injection state of the normal saline to the display 300. Further, the electronic device 100 may display an UI 720 indicating the injection of analgesic of 500 mL that has not yet been completed.

Figure 8:
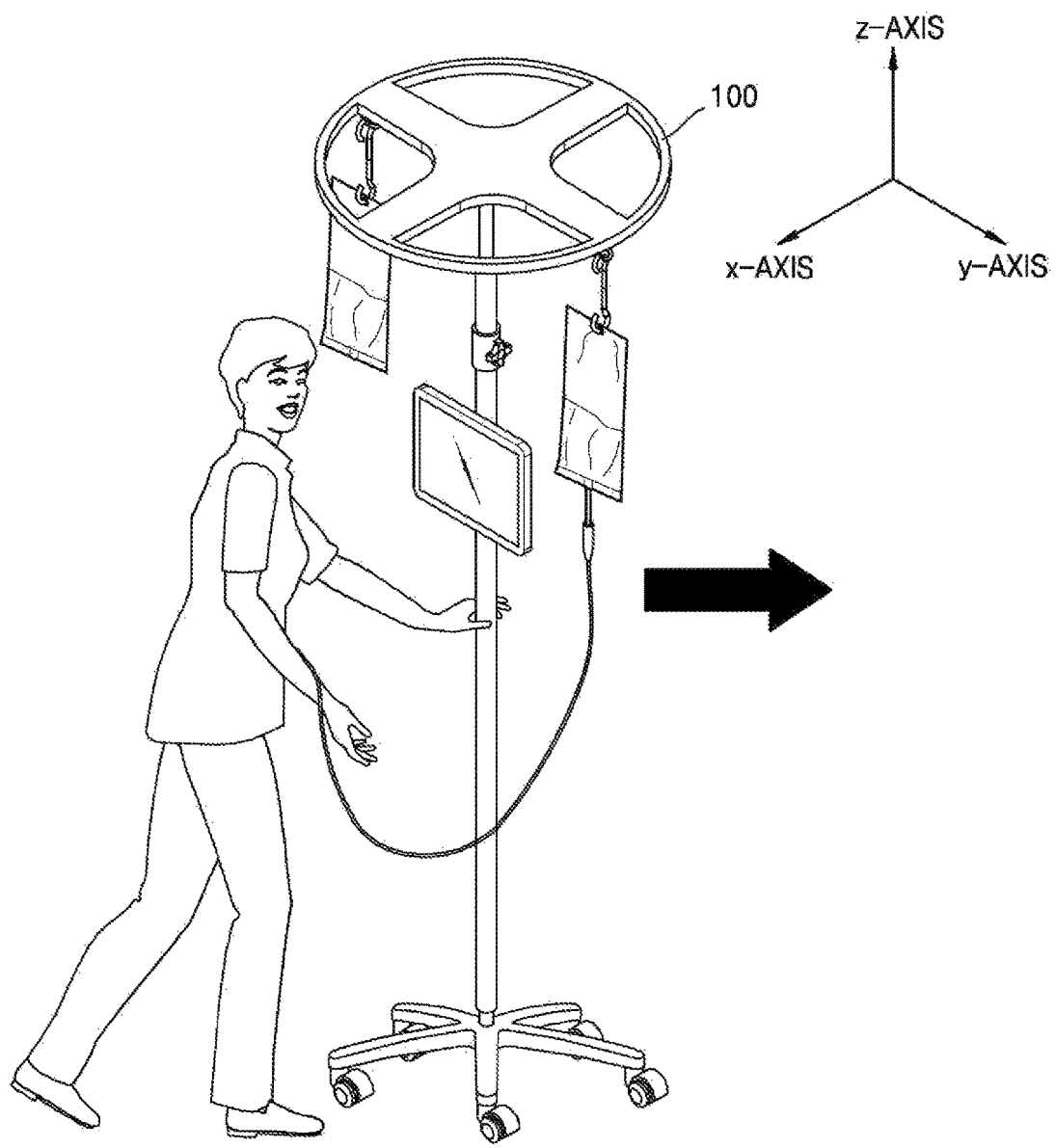
FIG. 8 is a diagram explaining a method by which an electronic device measures an amount of exercise performed by a user according to an example embodiment.

FIG. 8 is a diagram for explaining a method by which the electronic device 100 measures an amount of exercise of a user according to an example embodiment.

The electronic device 100 according to an example embodiment may sense the acceleration of the electronic device 100 to obtain acceleration data, and measure the amount of exercise of the user based on the obtained acceleration data.

For example, referring to FIG. 8, the electronic device 100 may sense the acceleration of the electronic device 100 when the electronic device 100 moves. Since an IV pole 10 moving together with the electronic device 100 moves by a wheel unit of the IV pole 10, there may be no movement in a z-axis direction. However, the number of steps of the user indicating the amount of exercise of the user may be measured based on the movement in the z-axis direction. Therefore, the electronic device 100 may measure acceleration $a_x$ in an x-axis direction and acceleration $a_y$ in a y-axis direction of the electronic device 100 using an acceleration sensor, and may calculate acceleration $a_z$ in the z-axis direction based on the measured acceleration $a_x$ and acceleration $a_y$.

Also, the electronic device 100 may calculate an acceleration variation $\Delta a_x$ in the x-axis direction for a unit time and an acceleration variation $\Delta a_y$ in the y-axis direction for the unit time, and an acceleration variation $\Delta a_z$ in the z-axis direction for the unit time based on the acceleration variation $\Delta a_x$ and the acceleration variation $\Delta a_y$.

The electronic device 100 according to an example embodiment may store the calculated acceleration variation $\Delta a_z$ in a buffer. At this time, the buffer may be a temporary storage space for storing the acceleration variation $\Delta a_z$ obtained for a predetermined time, and may include, for example, memory capable of storing the acceleration variation $\Delta a_z$ obtained for 10 seconds, but example embodiments are not limited thereto. The electronic device 100 may delete acceleration data stored in the order of oldest to be deleted first if there is no more space in the buffer.

The electronic device 100 may move with the user when the user moves, and the electronic device 100 may be temporarily moved without a movement of the user. The electronic device 100 may measure the amount of exercise of the user by distinguishing the case where the user moves and the case where the electronic device 100 is temporarily moved without the movement of the user.

The electronic device 100 according to an example embodiment may determine whether the number of the acceleration variation $\Delta a_z$ having a value equal to or greater than a threshold value is equal to or greater than a predetermined number, based on the acceleration variation $\Delta a_z$ stored in the buffer. The electronic device 100 may determine whether a size of the acceleration variation $\Delta a_z$ is greater than or equal to a threshold value to determine whether the movement of the electronic device 100 is caused by the movement of the user. The electronic device 100 may determine that the user is exercising when the size of the acceleration variation $\Delta a_z$ is greater than or equal to the threshold value.

Also, the electronic device 100 may determine whether the number of the acceleration variation $\Delta a_z$ having a value greater than the threshold value among the plurality of acceleration variations $\Delta a_z$ stored in the buffer is equal to or greater than a predetermined number. For example, the electronic device 100 may temporarily move by a temporary movement of the user, or by an external factor other than the user. If the electronic device 100 temporarily moves by the temporary movement of the user or the external factor, the acceleration variation $\Delta a_z$ having the value greater than the threshold value may be temporarily obtained, and the number of the acceleration variation $\Delta a_z$ having the value greater than the threshold value may be relatively small. However, when the electronic device 100 moves by the user continuously moving for a period over a predetermined time, the acceleration variation $\Delta a_z$ having a value greater than the threshold value may be continuously obtained, and the number of the acceleration variation $\Delta a_z$ having a value greater than the threshold value may be relatively large. Accordingly, the electronic device 100 may determine whether the user is exercising by measuring the number of the acceleration variation $\Delta a_z$ having a value greater than the threshold value.

The electronic device 100 according to an example embodiment may calculate a first point of time at which the number of the acceleration variation $\Delta a_z$ having a value greater than the threshold value among the plurality of acceleration variations $\Delta a_z$ stored in the buffer is equal to or greater than the predetermined number, and a second point of time at which the number of the acceleration variation $\Delta a_z$ having a value greater than the threshold value is less than the predetermined number. Then, the electronic device 100 may measure the amount of exercise of the user based on a difference between the second point of time and the first point of time.

The electronic device 100 according to an example embodiment may output a UI indicating the measured amount of exercise of the user on the display 300.

Figure 9:
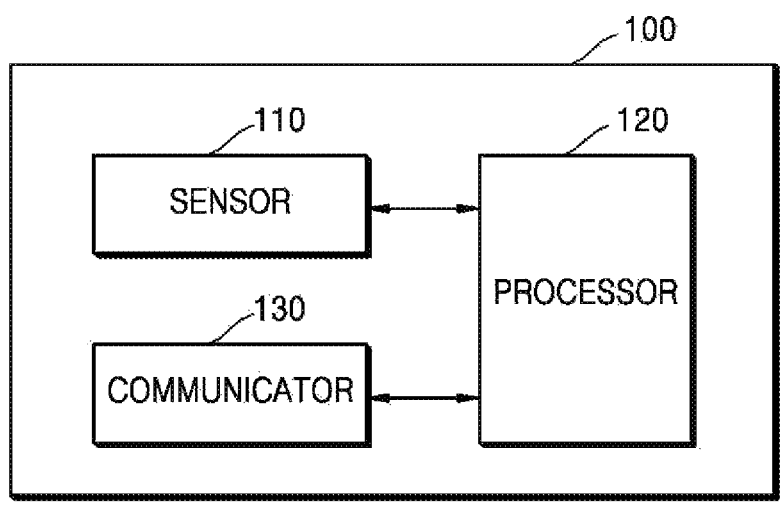
FIGS. 9 and 10 are block diagrams of a configuration of an electronic device according to an example embodiment.
Figure 10:
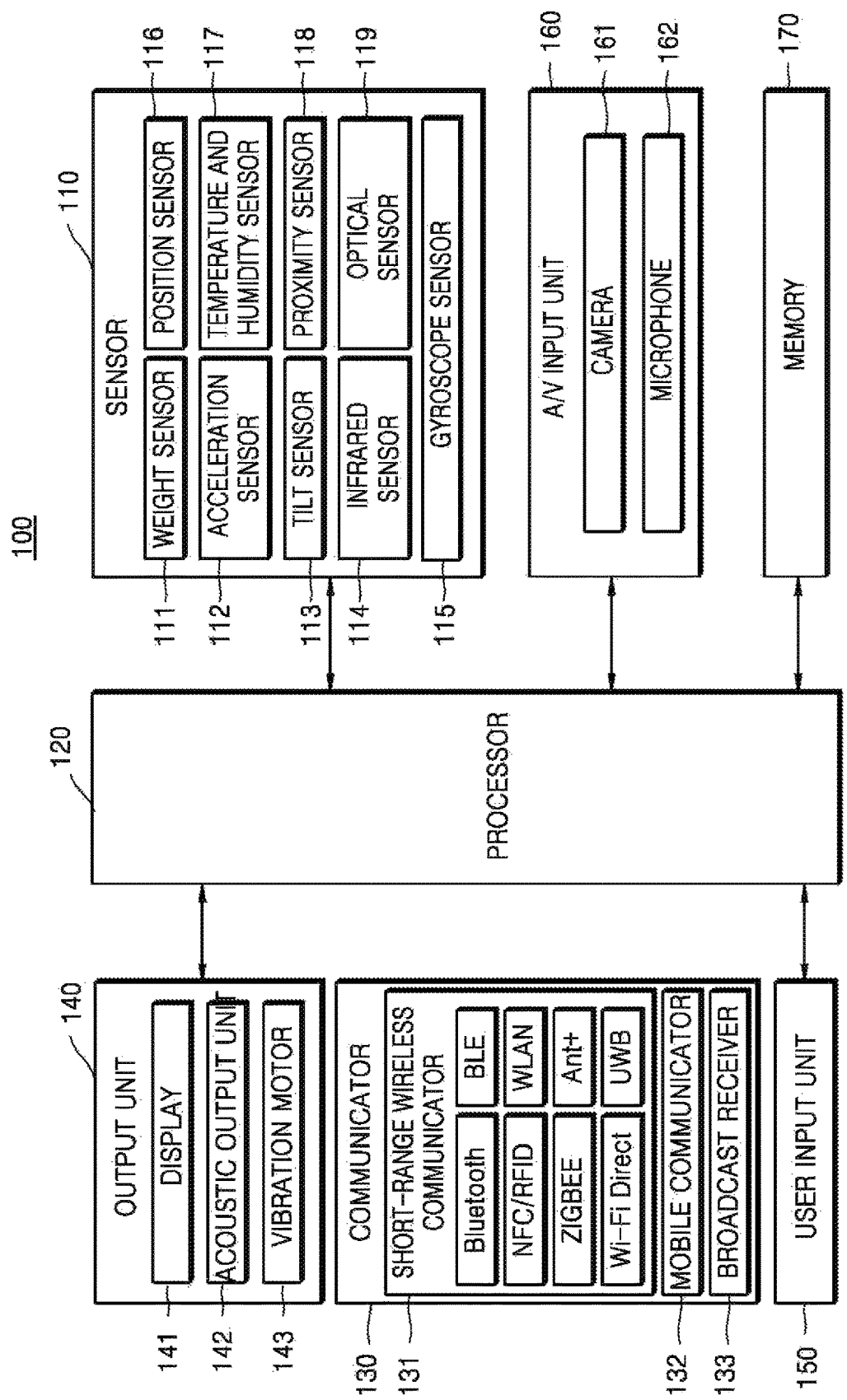

FIGS. 9 and 10 are block diagrams of a configuration of the electronic device 100 according to an example embodiments.

As shown in FIG. 9, the electronic device 100 according to an example embodiment may include a sensor 110, a processor 120, and a communicator 130. However, the electronic device 100 may include other components than components shown in FIG. 9. For example, as shown in FIG. 10, the electronic device 100 according to an example embodiment may further include an output unit 140, a user input unit 150, an A/V input unit 160, and a memory 170.

The sensor 110 may include at least one of the weight sensor 111, an acceleration sensor 112, a tilt sensor 113, an infrared sensor 114, a gyroscope sensor 115, a position sensor (e.g. a global positioning system (GPS)) 116, a temperature and humidity sensor 117, a proximity sensor 118, and an optical sensor 119, but example embodiments are not limited thereto.

The sensor 110 according to an example embodiment may sense a weight of an IV 11 connected to the electronic device 100 or a discharge liquid discharged from a user. For example, the weight sensor 111 may sense the weight of the IV 11 or the discharge fluid. For example, the weight sensor 111 may amplify a voltage variation value that varies depending on the weight of the IV 11 or the discharge liquid, convert the amplified variation value into a digital signal, and sense the weight of the IV 11 or the discharge liquid based on the converted digital signal.

Also, the sensor 110 according to an example embodiment may sense acceleration of the electronic device 100. For example, the acceleration sensor 112 may sense the acceleration of the electronic device 100 when the electronic device 100 moves.

The processor 120 may control an overall operation of the electronic device 100. For example, the processor 120 may generally control the sensor 110, the communicator 130, the output unit 140, the user input unit 150, the A/V input unit 160, and the memory 170, and the like by executing programs stored in the memory 170.

The processor 120 according to an example embodiment may measure the time remaining until an injection of the IV 11 is completed based on the sensed weight of the IV 11. For example, the processor 120 may calculate a rate at which the IV 11 is injected by measuring a variation in the weight of the IV 11 that varies over a unit time. Further, the processor 120 may measure the time remaining until the injection of the IV 11 is completed, based on the weight of the IV 11 and the injection rate of the IV 11.

The processor 120 according to an example embodiment may determine whether the time remaining until the injection of the IV 11 is completed is equal to or less than a predetermined value. When the injection of the IV 11 is completed, a medical staff may need to remove the IV 11 connected to the electronic device 100. Therefore, if the time remaining until the injection of the IV 11 is completed is equal to or less than the predetermined value, it may be necessary to inform the medical staff the time left for removing the IV 11. The predetermined value may vary depending on an internal setting or an external setting of the electronic device 100. For example, the predetermined value may be set to 5 minutes, and the electronic device 100 may determine whether the time remaining until the injection of the IV 11 is completed is 5 minutes or less, but example embodiments are not limited thereto.

Also, the processor 120 according to an example embodiment may measure an amount of exercise of the user based on acceleration data obtained by the sensor 110. Also, the processor 120 according to an example embodiment may sense the weight of the discharge liquid discharged from the user as well as the weight of the IV 11 injected to the user, and determine whether the weight of the discharge liquid is equal to or greater than a predetermined value.

Also, the processor 120 according to an example embodiment may control the communicator 130 to transmit an alarm signal indicating an injection state of the IV 11 to the external device 101, based on a determination result. For example, the processor 120 may determine that the time remaining until the injection of the IV 11 is completed is equal to or less than the predetermined value, and control the communicator 120 to transmit the alarm signal to the external device 101.

The communicator 130 may include one or more components for communicating between the electronic device 100 and the external device 101 or between the electronic device 100 and a server. For example, the communicator 130 may include a short-range communicator 131, a mobile communicator 132, and a broadcast receiver 133.

The short-range wireless communicator 131 may include a Bluetooth communicator, a Bluetooth Low Energy (BLE) communicator, a Near Field Communicator, a WLAN communicator, a Zigbee communicator, an infrared data association (IrDA) communicator, a Wi-Fi Direct (WFD) communicator, an ultra wideband (UWB) communicator, and an Ant+communicator, etc. But example embodiments are not limited thereto.

The mobile communicator 132 may transmit and receive a wireless signal to and from, for example, at least one of a base station, an external terminal, and the server on a mobile communication network. The wireless signal may include various types of data depending on a voice call signal, a video call signal, or a text/multimedia message transmission/reception.

The broadcast receiver 133 may receive broadcast signals and/or broadcast-related information from outside through a broadcast channel. The broadcast channel may include a satellite channel and a terrestrial channel.

The communicator 130 according to an example embodiment may determine that the time remaining until the injection of the IV 11 connected to the electronic device 100 is completed is equal to or less than the predetermined value, and transmit an alarm signal indicating the injection state of the IV 11 to the external device 101. Also, the communicator 130 may receive prescription information of the user from the server.

The output unit 140 may be used to output an audio signal, a video signal, or a vibration signal and may include a display 141, an audio output unit 142, a vibration motor 143, and the like.

The display 141 according to an example embodiment may output a UI indicating a status of an operation performed by the electronic device 100. For example, when an IV 11 is connected to the electronic device 100 and the time remaining until the injection of the IV 11 is completed is measured based on a result of sensing the weight of the IV 11, the display 141 may output the UI indicating the time remaining until the injection of the IV 11 is completed. Further, the display 141 may output a UI indicating a type of the IV 11 recognized based on the prescription information of the user.

The display 141 according to an example embodiment may output a message informing that the injection has been completed when the injection of the IV 11 is completed, and may also output a message informing that the medical staff has been called.

The sound output unit 142 may output audio data received from the communicator 130 or stored in the memory 170. Also, the sound output unit 142 may output an acoustic signal related to a function (for example, a notification sound) performed by the electronic device 100. The sound output unit 1112 may include a speaker, a buzzer, and the like.

The vibration motor 143 may output a vibration signal. For example, the vibration motor 143 may output the vibration signal corresponding to an output of the alarm signal. Also, the vibration motor 143 may output a vibration signal when a touch is input by a user on a touch screen. The vibration motor 143 may output the vibration signal when the injection of the IV 11 is completed or when a drain bag is filled with the discharge liquid of a weight equal to a greater than a predetermined value.

The user input unit 150 refers to an interface for the user to input data for controlling the electronic device 100. For example, the user input unit 150 may include a key pad, a dome switch, a touch pad (a capacitive overlay touch pad, a resistive overlay touch pad, an infrared (IR) beam touch pad, a surface acoustic wave touch pad, an integral strain gauge touch pad, a piezoelectric touch pad, or the like), a jog wheel, a jog switch, and the like, but example embodiments are not limited thereto.

The audio/video (A/V) input unit 160 may be used to input an audio signal or a video signal, and may include a camera 161, a microphone 162, and the like.

The microphone 162 may receive an external acoustic signal and process the acoustic signal to electrical voice data. For example, the microphone 162 may receive the acoustic signal from the external device 101 or the user. The microphone 162 may use various noise removal algorithms to remove noise generated while receiving the external acoustic signal.

The memory 170 may store a program for processing and controlling the processor 120 and may store input/output data (e.g., the prescription information of the user, data measuring the time remaining until the injection of the IV 11 is completed, weight data of the IV 11, acceleration data of the electronic device 100, and the like).

The memory 170 may include at least one type of storage medium from among a flash memory type memory, a hard disk type memory, a multimedia card micro type memory, a card type memory (e.g., a secure digital (SD) or extreme digital (XD) memory), random access memory (RAM), static RAM (SRAM), read only memory (ROM), electrically erasable programmable ROM (EEPROM), PROM, a magnetic memory, a magnetic disc, and an optical disc.

Example embodiments may be implemented in a form of a recording medium including computer-executable instructions such as a program module executed by a computer system. A non-transitory computer-readable medium may be an arbitrary available medium which may be accessed by a computer system and may include all types of volatile and non-volatile media and separated and non-separated media. Also, the non-transitory computer-readable medium may include all types of computer storage media and communication media. The computer storage media may include all types of volatile and non-volatile and separated and non-separated media implemented by an arbitrary method or technique for storing information such as computer-readable instructions, a data structure, a program module, or other data. The communication media may include computer-readable instructions, a data structure, a program module, other data of a modulated signal such as a carrier, other transmission mechanism, and arbitrary information delivery media.

The terms "unit" and "interface" may indicate a hardware component such as a processor or a circuit and/or a software component executed by a hardware component such as a processor.

While example embodiments have been described with reference to the figures, it will be understood by those of ordinary skill in the art that various changes in form and details may be made therein without departing from the spirit and scope of the present disclosure, as defined by the following claims, and their equivalents.

What is claimed is:

1. A method of operating an electronic device, the method comprising:
   sensing an initial weight of an intravenous (IV) fluid and a weight of the IV fluid in a predetermined period;
   measuring a time remaining until injection of the IV fluid is completed, based on the sensed weights of the IV fluid;
   determining whether the measured remaining time is equal to or less than a predetermined value; and
   transmitting an alarm signal indicating an injection state of the IV fluid to an external device in response to the measured remaining time being determined to be equal to or less than the predetermined value.

2. The method of claim 1, further comprising:
   receiving prescription information with respect to the user from a server; and
   determining a type of the IV fluid by comparing the received prescription information and the sensed initial weight of the IV fluid.

3. The method of claim 2, wherein the received prescription information comprises a plurality of IV fluids prescribed to the user, and
   wherein the determining of the type of the IV fluid comprises, among the plurality of IV fluids from the received prescription information, in response to an external input of selecting one of two or more IV fluids having the same weight as the sensed weight of the IV fluid injected into the user, determining the type of the IV fluid injected into the user as the selected IV fluid.

4. The method of claim 1, further comprising outputting a user interface (UI) indicating information about the injection state of the IV fluid.

5. The method of claim 1, further comprising:
   obtaining acceleration data by sensing acceleration of the electronic device;
   determining whether a number of pieces of acceleration data having a magnitude equal to or greater than a threshold value among a plurality of pieces of acceleration data obtained during a predetermined time is equal to or greater than a predetermined number; and measuring an amount of exercise performed by the user based on the number of pieces of acceleration data determined to have a magnitude equal to or greater than the predetermined number.

6. The method of claim 5, wherein the measuring of the amount of exercise performed by the user comprises:

measuring the amount of exercise performed by the user based on a difference between a first point in time at which the number of pieces of acceleration data having the magnitude equal to or greater than the threshold value is equal to or greater than the predetermined number, and a second point in time at which the number of pieces of acceleration data having the magnitude equal to or greater than the threshold value is less than the predetermined number.

7. The method of claim 1, further comprising:

sensing a weight of a discharge liquid discharged from the user;

determining whether the sensed weight of the discharge liquid is equal to or greater than a predetermined weight; and transmitting an alarm signal indicating a discharge state of the discharge liquid to the external device based on the sensed weight of the discharge liquid being determined to be equal to or greater than the predetermined weight.

8. A non-transitory computer-readable recording medium having recorded thereon a program for executing the method of operating the electronic device of claim 1 on a computer.

9. An electronic device comprising:

a sensor configured to sense an initial weight of an intravenous (IV) fluid and a weight of the IV fluid in a predetermined period;

a communicator; and a processor configured to measure a time remaining until injection of the IV fluid is completed based on the sensed weights of the IV fluid, determine whether the measured remaining time is equal to or less than a predetermined value, and control the communicator to transmit an alarm signal indicating an injection state of the IV fluid to an external device in response to the measured time being determined to be equal to or less than the predetermined value.

10. The electronic device of claim 9, wherein the processor is further configured to control the communicator to receive prescription information with respect to the user from a server, and determine a type of the IV fluid by comparing the received prescription information and the sensed initial weight of the IV fluid.

11. The electronic device of claim 10, wherein the received prescription information comprises a plurality of IV fluids prescribed to the user, and wherein the processor is further configured to, among the plurality of IV fluids included in the received prescription information, in response to an external input of selecting one of two or more IV fluids having the same weight as the sensed weight of the IV fluid injected into the user, determine the type of the IV fluid injected into the user as the selected IV fluid.

12. The electronic device of claim 9, further comprising a display configured to output a user interface (UI) indicating information about the injection state of the IV fluid.

13. The electronic device of claim 9, wherein the sensor is further configured to obtain acceleration data by sensing acceleration of the electronic device, and wherein the processor is further configured to determine whether a number of pieces of acceleration data having a magnitude equal to or greater than a threshold value among a plurality of pieces of acceleration data obtained during a predetermined time is equal to or greater than a predetermined number, and measure an amount of exercise performed by the user based on the number of pieces of acceleration data determined to have a magnitude equal to or greater than the predetermined number.

14. The electronic device of claim 13, wherein the processor is further configured to measure the amount of exercise performed by the user based on a difference between a first point in time at which the number of pieces of acceleration data having the magnitude equal to or greater than the threshold value is equal to or greater than the predetermined number, and a second point in time at which the number of pieces of acceleration data having the magnitude equal to or greater than the threshold value is less than the predetermined number.

15. The electronic device of claim 9, wherein the sensor is further configured to sense a weight of a discharge liquid discharged from the user, and wherein the processor is further configured to determine whether the sensed weight of the discharge liquid is equal to or greater than a predetermined weight, and transmit an alarm signal indicating a discharge state of the discharge liquid to the external device in response to the sensed weight of the discharge liquid being determined to be equal to or greater than the predetermined weight.

* * * * *